USOO9572409B2

(12) United States Patent
Pidgeon et al.

(10) Patent No.: US 9,572,409 B2
(45) Date of Patent: Feb. 21, 2017

(54) CARRYING BAG

(71) Applicant: SMITH & NEPHEW PLC, London (GB)

(72) Inventors: Andrew Pidgeon, Cambridgeshire (GB); Richard Mann, Cambridge (GB)

(73) Assignee: SMITH & NEPHEW PLC, London (GB)

( * ) Notice: Subject to any disclaimer, the term of this patent is extended or adjusted under 35 U.S.C. 154(b) by 77 days.

(21) Appl. No.: 13/728,236

(22) Filed: Dec. 27, 2012

(65) Prior Publication Data

US 2013/0180876 A1 Jul. 18, 2013

Related U.S. Application Data

(60) Division of application No. 13/570,953, filed on Aug. 9, 2012, now Pat. No. 8,413,812, which is a (Continued)

(30) Foreign Application Priority Data

Jul. 2, 2007 (GB) .................................. 0712764.0

(51) Int. Cl.
*A61B 17/06* (2006.01)
*A45C 11/00* (2006.01)
(Continued)

(52) U.S. Cl.
CPC .............. *A45C 11/00* (2013.01); *A45F 5/021* (2013.01); *A61M 1/0031* (2013.01);
(Continued)

(58) Field of Classification Search
CPC .......................... A45C 11/00; A45C 2005/035
(Continued)

(56) References Cited

U.S. PATENT DOCUMENTS 3,115,138 A 12/1963 McElvenny et al.
3,295,576 A * 1/1967 Schmitt et al. ............ 206/316.2
(Continued)

FOREIGN PATENT DOCUMENTS

DE 1000684 B 1/1957
DE 3431426 A1 7/1985
(Continued)

OTHER PUBLICATIONS

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96.
(Continued)

*Primary Examiner* — Anthony Stashick
*Assistant Examiner* — Raven Collins
(74) *Attorney, Agent, or Firm* — Knobbe Martens Olson & Bear LLP

(57) ABSTRACT

A carrying case (500) and handle (504) for accommodating a portable topical negative pressure therapy apparatus (200) comprising a device (202) and a waste canister (204) separable therefrom, the waste canister having an aspiration conduit (274) emerging therefrom is described, the carrying bag comprising an apparatus receiving pouch (502), said pouch having opening and closing means (522, 524) at a lower portion thereof and said handle (504) being directly attached to said apparatus.

26 Claims, 9 Drawing Sheets

Related U.S. Application Data continuation of application No. 12/667,230, filed as application No. PCT/BG2008/050512 on Jun. 27, 2008, now Pat. No. 8,240,470.

(51) Int. Cl.
| | | |
|---|---|---|
| *A45F 5/02* | (2006.01) | |
| *A61M 1/00* | (2006.01) | |
| *A45C 3/00* | (2006.01) | |
| *A45C 13/26* | (2006.01) | |

(52) U.S. Cl.
CPC ............. *A61M 1/0088* (2013.01); *A45C 3/00* (2013.01); *A45C 13/26* (2013.01); *A61M 2205/3331* (2013.01); *A61M 2205/3334* (2013.01); *A61M 2205/3382* (2013.01); *A61M 2209/088* (2013.01)

(58) Field of Classification Search
USPC .......... 206/348, 316.1, 316.2, 320, 578, 183
See application file for complete search history.

(56) References Cited

U.S. PATENT DOCUMENTS

| | | | |
|---|---|---|---|
| 4,382,441 A | 5/1983 | Svedman | |
| 4,569,674 A | 2/1986 | Phillips | |
| 4,649,973 A * | 3/1987 | Uchin | 206/316.2 |
| 4,710,165 A | 12/1987 | McNeil et al. | |
| 4,767,417 A | 8/1988 | Boehringer | |
| 4,930,997 A | 6/1990 | Bennett | |
| 4,969,880 A | 11/1990 | Zamierowski | |
| 5,134,994 A | 8/1992 | Say | |
| 5,172,838 A * | 12/1992 | Rowell | A45C 11/38 190/103 |
| 5,176,663 A | 1/1993 | Svedman | |
| 5,358,494 A | 10/1994 | Svedman | |
| 5,466,229 A | 11/1995 | Elson | |
| 5,527,293 A | 6/1996 | Zamierowski | |
| 5,636,643 A | 6/1997 | Argenta | |
| 5,645,081 A | 7/1997 | Argenta | |
| D408,625 S | 4/1999 | Barker | |
| 5,907,721 A * | 5/1999 | Schelling et al. | 396/27 |
| D414,925 S * | 10/1999 | Holland | D3/218 |
| 6,071,267 A | 6/2000 | Zamierowski | |
| 6,142,982 A | 11/2000 | Hunt | |
| 6,279,804 B1 | 8/2001 | Gregg | |
| 6,390,345 B1 | 5/2002 | Brown et al. | |
| 6,398,767 B1 | 6/2002 | Fleischmann | |
| 6,648,862 B2 | 11/2003 | Watson | |
| 6,752,794 B2 | 6/2004 | Lockwood | |
| 6,755,807 B2 | 6/2004 | Risk, Jr. | |
| 6,764,462 B2 | 7/2004 | Risk, Jr. | |
| 6,824,533 B2 | 11/2004 | Risk, Jr. | |
| 6,936,037 B2 | 8/2005 | Bubb | |
| 6,948,614 B1 * | 9/2005 | Hall | A45C 11/329 150/154 |
| 6,957,738 B2 | 10/2005 | Hammond | |
| 7,004,915 B2 | 2/2006 | Boynton | |
| 7,022,113 B2 | 4/2006 | Lockwood | |
| 7,077,832 B2 | 7/2006 | Fleischmann | |
| 7,108,683 B2 | 9/2006 | Zamierowski | |
| 7,195,624 B2 | 3/2007 | Lockwood | |
| 7,198,046 B1 | 4/2007 | Argenta | |
| 7,216,651 B2 | 5/2007 | Argenta | |
| D543,691 S | 6/2007 | Payne et al. | |
| D545,055 S | 6/2007 | Lieberman et al. | |
| D548,954 S | 8/2007 | Andersen et al. | |
| D556,444 S | 12/2007 | Ipsen et al. | |
| 7,438,705 B2 | 10/2008 | Karpowicz | |
| D587,901 S | 3/2009 | Pidgeon | |
| 7,524,315 B2 | 4/2009 | Blott | |
| 7,534,240 B1 | 5/2009 | Johnson | |
| D602,582 S | 10/2009 | Pidgeon | |
| D602,583 S | 10/2009 | Pidgeon | |
| D602,584 S | 10/2009 | Pidgeon | |
| D607,202 S | 1/2010 | Pidgeon | |
| 7,678,090 B2 | 3/2010 | Risk, Jr. | |
| 7,694,814 B1 | 4/2010 | Cristobal et al. | |
| D617,094 S | 6/2010 | Pidgeon | |
| 8,843,327 B2 | 9/2014 | Vernon-Harcourt et al. | |
| 8,945,073 B2 | 2/2015 | Croizat et al. | |
| 2002/0198503 A1 | 12/2002 | Risk, Jr. | |
| 2003/0050594 A1 | 3/2003 | Zamierowski | |
| 2005/0177190 A1 | 8/2005 | Zamierowski | |
| 2005/0247732 A1 * | 11/2005 | Duke | 222/183 |
| 2007/0023453 A1 * | 2/2007 | Simkins | 222/183 |
| 2007/0038172 A1 | 2/2007 | Zamierowski | |
| 2007/0131573 A1 | 6/2007 | Boyles | |
| 2007/0193902 A1 | 8/2007 | Myers et al. | |
| 2008/0200905 A1 | 8/2008 | Heaton | |
| 2009/0012482 A1 | 1/2009 | Pinto | |
| 2009/0076467 A1 | 3/2009 | Pinto | |
| 2009/0254066 A1 | 10/2009 | Heaton | |
| 2009/0270820 A1 | 10/2009 | Johnson | |

FOREIGN PATENT DOCUMENTS

| | | |
|---|---|---|
| DE | 20301859 U1 | 6/2003 |
| EP | 0777504 B1 | 10/1998 |
| EP | 2 319 476 A2 | 5/2011 |
| FR | 1163907 | 10/1958 |
| GB | 2037150 A | 7/1980 |
| GB | 1575266 | 9/1980 |
| GB | 2195255 A4 | 4/1988 |
| GB | 2307180 A | 5/1997 |
| SU | 1251912 A1 | 4/1983 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 03/074106 A | 9/2003 |
| WO | WO 2004/037334 | 5/2004 |
| WO | WO 2005/004670 | 1/2005 |
| WO | WO 2005/105180 | 11/2005 |
| WO | WO 2007/013064 A | 2/2007 |
| WO | WO 2007/024230 A | 3/2007 |
| WO | WO 2007/030599 A | 3/2007 |

OTHER PUBLICATIONS

Karev, I.D., et al., "Foam Drainage System for Treating Purulent Wounds," in Second All-Union Conference "Wounds and Wound Infections" (Presentation Abstracts) (Moscow, USSR 1986) pp. 87-88.

Kuznetsov, V.A. Bagautdinov, N.A., "Vacuum and Vacuum-Sorption Treatment of Open Septic Wounds," in Second All-Union Conference "Wounds and Wound Infections" (Presentation Abstracts) (Moscow, USSR 1986) pp. 91-21.

Chariker, M.E. et al. "Effective Management of Incisional and Cutaneous Fistulae with Close Suction Wound Drainage" *Contemporary Surgery* 1989 34:59-63.

Jeter, K. "Managing Draining wounds and Fistulae: New and Established Methods" Chronic Wound Care pp. 240-246.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987.

Solovev, V.A., "Treatment and Prevention of Suture Failures after Gastric Resection" (Dissertation Abstract) (S.M. Kirov Gorky State Medical Institute, Gorky USSR 1988).

Svedman, P. "A Dressing Allowing Continuous Treatment of a Biosurface" *IRCS Med. Science: Biomed. Tech.; Clinic. Med., Surg. and Transplantation* 1979 7:221.

Svedman, P. "Irrigation of Treatment of Leg Ulcers" *The Lancet* 1983 pp. 532-534.

Svedman, P. "Irrigation Treatment in Split-Thickness Skin Grafting of Intractable Leg Ulcers" *Scand. J. Plast. Reconst. Surg.* 1985 19:211-213.

(56) References Cited

OTHER PUBLICATIONS

Svedman, P. et al. "A Dressing System Providing Fluid Supply and Suction Drainage Used for Continuous or Intermittent Irrigation" *Annals of Plastic Surgery* 1986 17(2):125-133.
International Search Report mailed Nov. 11, 2008 in PCT/GB2008/050512 in 4 pages.
International Preliminary Report on Patentability issued Jan. 5, 2010 in PCT/GB2008/050512 in 7 pages.

\* cited by examiner

CARRYING BAG

CROSS-REFERENCE TO RELATED APPLICATIONS

This application is divisional of U.S. application Ser. No. 13/570,953, filed Aug. 9, 2012, which is a continuation application of U.S. application Ser. No. 12/667,230, filed Dec. 29, 2009, now U.S. Pat. No. 8,240,470, which is the national stage application of PCT/GB2008/050512, filed Jun. 27, 2008, which claims priority to Great Britain Patent Application No. 0712764.0, filed Jul. 2, 2007. The disclosures of these prior applications are incorporated by reference in their entirety and should be considered a part of this specification.

BACKGROUND OF THE INVENTION

1. Field of the Invention

The present invention relates to apparatus and a method for the application of topical negative pressure (TNP) therapy to wounds. In particular, but not exclusively, the present invention relates to a bag to facilitate use, carrying and portability of such apparatus.

2. Description of the Related Art

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to a belt or harness. The apparatus shown in this reference is divided into two separate items: a first item comprising a TNP therapy device and waste canister; and, a second item comprising a battery power pack for the TNP device. The two items are worn on a belt or harness by the patient on their left and right sides. This arrangement is inconvenient and cumbersome and necessitates a power lead connection between the two items providing a further potential source of inconvenience and failure. Furthermore, the apparatus of this reference is not covered or hidden in any way and may constitute a potential source of embarrassment to a user or wearer. Since the device and waste canister are held close to the user's body by the belt or harness it may be necessary to remove the device and waste canister unit either from the belt or harness or the belt and harness from the user's body to allow the necessary room and freedom to be able change the waste canister for a fresh item when needed. If a user of the apparatus described in this document wishes to sit down or lie down then the belt or harness must be removed and placed safely on a surface before doing so.

It is an aim of the present invention to remove or at least partly mitigate at least some of the above-mentioned problems.

It is an aim of embodiments of the present invention to provide a lightweight and convenient means of carrying TNP therapy apparatus as described hereinbelow.

It is a further aim to provide such carrying means which facilitate replacing a full waste canister for a fresh one as easily and as inconspicuously as possible.

SUMMARY

According to a first aspect of the present invention there is provided a carrying case and handle for accommodating a portable topical negative pressure therapy apparatus comprising a device and a waste canister separable therefrom, the waste canister having an aspiration conduit connected thereto, the carrying bag comprising an apparatus receiving pouch, said pouch having opening and closing means at a lower portion thereof and said handle being directly attached to said apparatus.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and handle in the form of a short carry handle or a shoulder strap or harness, for example. The carry case may be adapted to conform to the shape of the apparatus comprised in the joined together device and waste canister. In particular, the carry case may be provided with a bottom opening portion to permit the waste canister to be changed without complete removal of the apparatus form the carry case.

In the carrying case according to the present invention there is a lower portion having an openable and closable aperture or opening, "lower portion" being defined as a lower part of the apparatus and carry case when it is being carried or worn by a user who is in a generally upright position when walking, standing or sitting, for example.

The apparatus comprising the device (as defined hereinabove) and the waste canister may be inserted into the carrying case pouch from the lower opening with the waste canister lowermost. The lower opening may have suitable means to open and close it such as zips, Velcro-type (trade name) material fastenings, press studs, magnets, for example. Aptly the opening and closing means may leave a small aperture open, generally at a position corresponding to the entry point of the aspiration conduit to the waste canister. Thus, in one embodiment of the carrying case and handle according to the present invention the opening and closing means may be in two parts if, for example, zips are used as the opening and closing means.

Whilst the lower opening allows for initial insertion of the apparatus into the carrying case it is primarily required to allow access by a user to the waste canister to permit changing for a fresh unit. The waste canister may be connected in use of the TNP therapy apparatus to the device by releasable clips bridging an interface between the device and canister, for example. Thus, the lower opening should be at least co-extensive with the releasable clips or able to be opened sufficiently widely or sufficiently far around the periphery of the carrying case by the opening and closing means to permit easy access to the releasable clips by the user. Thus, when the lower opening is opened for canister changing, an important feature of the present invention is that the handle is connected directly to the device unit of the apparatus otherwise it is possible that the whole apparatus might slide out of the carrying case. Where the handle is in the form of a shoulder strap worn over the user's shoulder or around the neck then the device and carrying case are securely retained together on the user allowing the user to quickly and conveniently access the waste canister for changing purposes without fear of the device being dropped. The aspiration conduit may be disconnected from a connector, for example, at the dressing end, the releasable clips securing the waste canister to the device released, the waste canister removed from the device and disposed of, perhaps temporarily in a sealable bag before final disposal in an appropriate receptacle, and a fresh canister substituted.

The apparatus retaining pouch of the carrying case may have a suitable aperture or apertures therein to allow the handle to pass therethrough and be attached to the device of the apparatus. The carry case may have upper openings to allow the carry handle (attached to the apparatus) to be pulled through.

The carry case may be provided with a clear window panel portion on a front face thereof to enable a user to see an LCD screen and operate control buttons or a keypad on the front of the device unit for varying the therapy applied by the apparatus. Such clear panel portion may be optionally coverable with a flap portion which can be pulled down to view and operate controls on the device. Such a flap portion may be held in place by any suitable means such as Velcro-type (trade name) fastening material or magnets, for example.

The carry case may be further provided with a second clear window panel portion coinciding with the position of the waste canister in order for a user to make a rough estimate of when the canister may need changing. The second flap portion may again be fixed in place covering the waste canister by similar means to the flap portion covering the controls of the device.

The flap portions referred to above may in alternative embodiments of the carrying case and handle of the present invention simply cover open apertures which coincide with the relevant areas of the device and waste canister.

The flaps may be mainly provided to hide the apparatus from the view of people other than the user so as to minimise any potential embarrassment to the user.

The carrying case may further comprise a pocket portion for accommodating spare equipment such as a spare aspiration conduit and/or a bag for receiving a used full waste canister for later disposal, for example. Such a pocket portion may conveniently be sited on a rear face of the pouch adjacent a user's body in use.

The carrying case may also be provided with a support loop on a rear face thereof to receive a user's belt if the user particularly wishes this means of support.

In embodiments of the device itself visual indication may be made of the status of the apparatus such as by an LED, for example. Aptly the carrying case pouch may have an aperture or clear window therein coinciding with a position of such visual indicator so that it may be seen at all times.

Other apertures in the carrying case pouch may be provided to coincide with the positions of such things as a battery charging socket and an exhaust port from which gaseous aspirated fluid is finally exhausted to atmosphere.

The handle may be a multi-purpose handle and may have two relatively short portions each connected to the device and able to be joined together at their free ends in order to form a short carry handle to be gripped by a hand of the user. Alternatively, the handle may be made longer by a third, centre portion which may be joined between the free ends of the shorter portions in order to form a longer shoulder strap to support the apparatus.

Aptly the handle may be attached to the device in such a manner that it is easily removable for cleaning.

The carry case and handle may be made from appropriate and easily cleaned material such as woven Nylon (trade name), vinyl type materials, polyethylene, silicone and moulded structures from plastics materials are also a possibility, for example.

Advantages of the carrying case and handle according to the present invention include the fact that if the wearer wishes to sit down or lie down then the apparatus in its carrying case merely needs to be taken from around the neck of the user and placed on a flat surface. Further, if the pouch portion becomes soiled, the apparatus may merely be removed therefrom since the handle is fixed to the apparatus and continue to be worn whilst the pouch portion is cleaned. The pouch portion may be very lightweight since virtually all of the weight of the apparatus is born by the handle.

BRIEF DESCRIPTION OF THE DRAWINGS

In order that the present invention may be more fully understood, examples will now be described by way of illustration only with reference to the accompanying drawings, of which.

DETAILED DESCRIPTION

Figure 1:
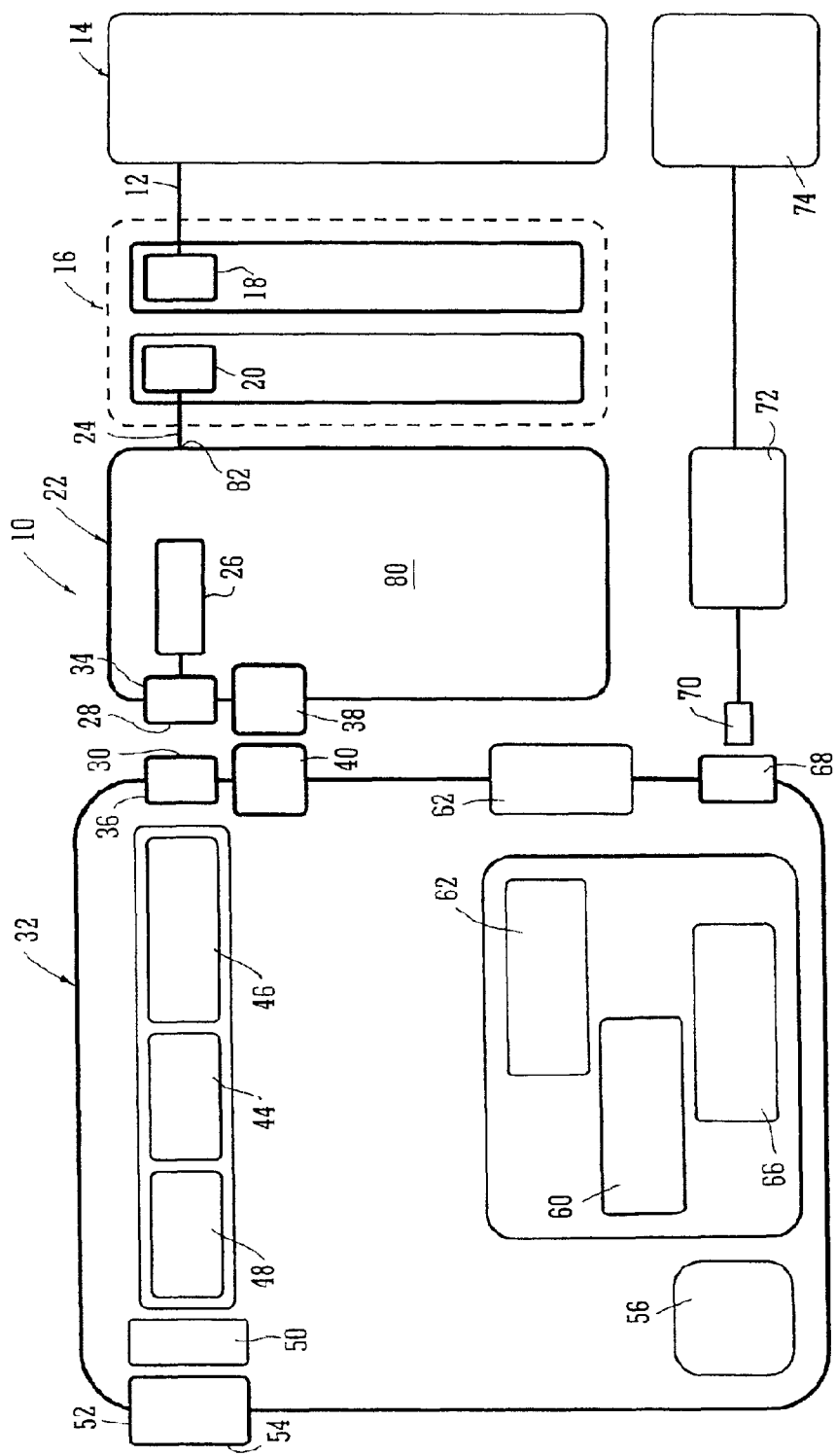
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µm hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
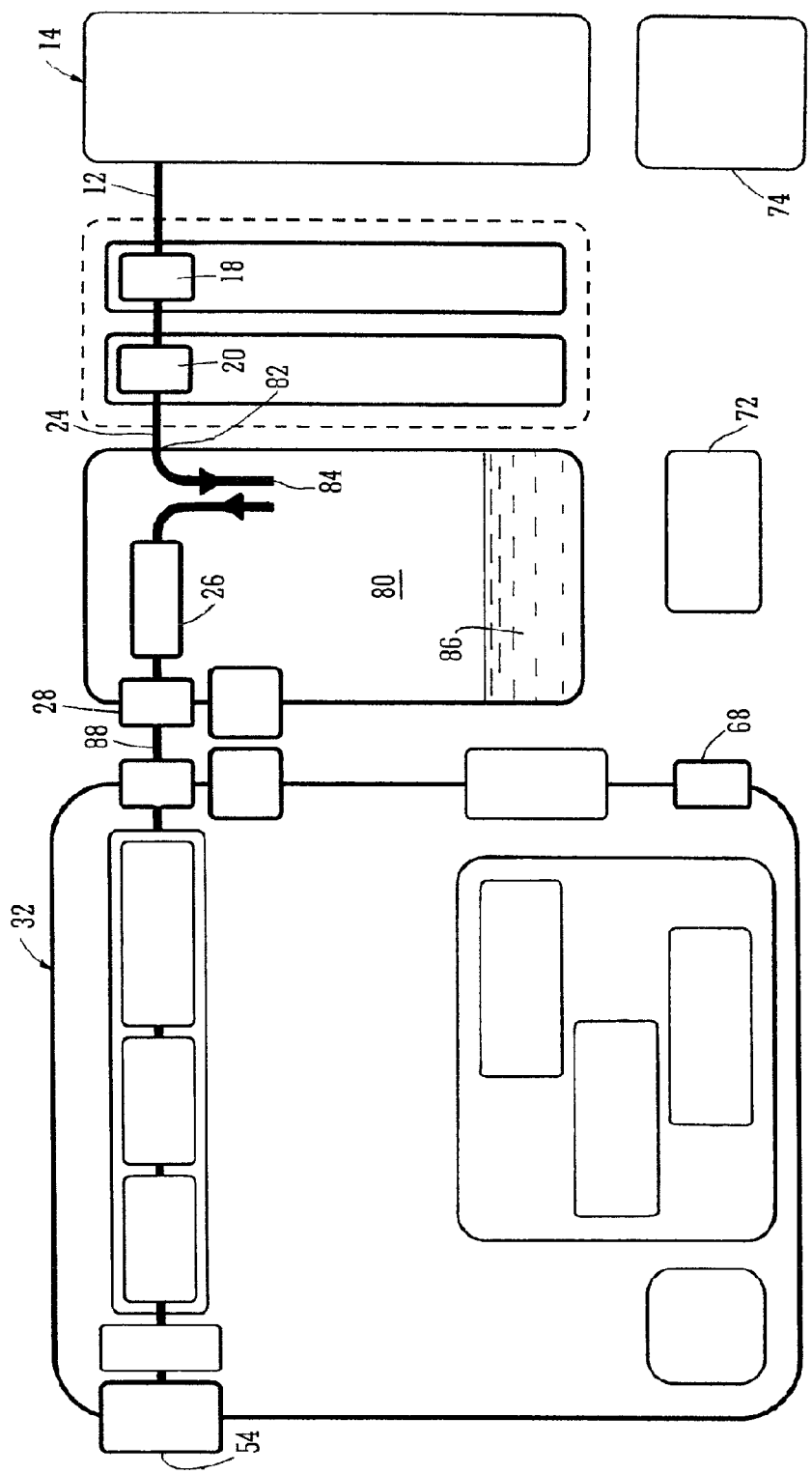
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
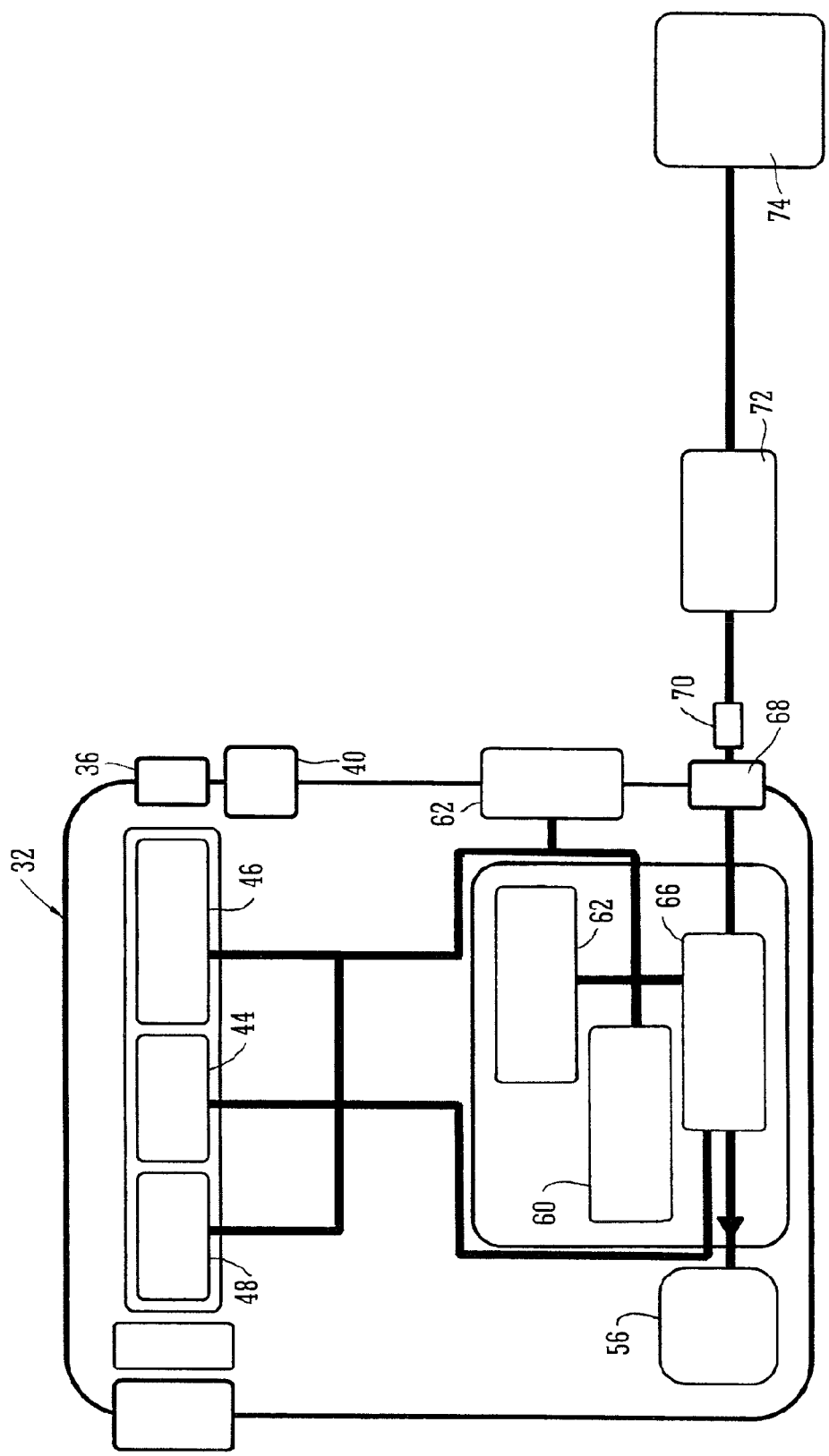
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
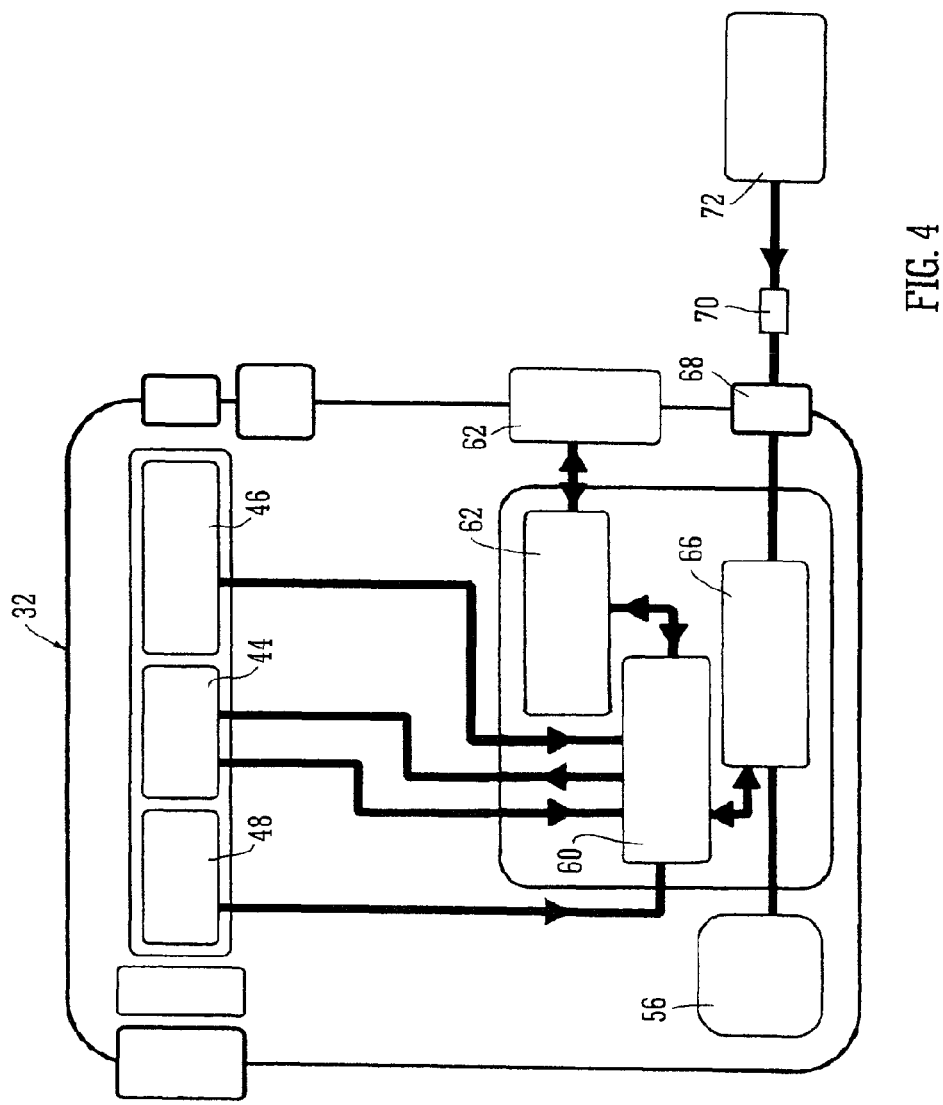
FIG. 4 shows a similar generalised schematic block diagram to FIG. 3 of the device unit and showing control system data paths for controlling the various functions and components of the apparatus.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 7:
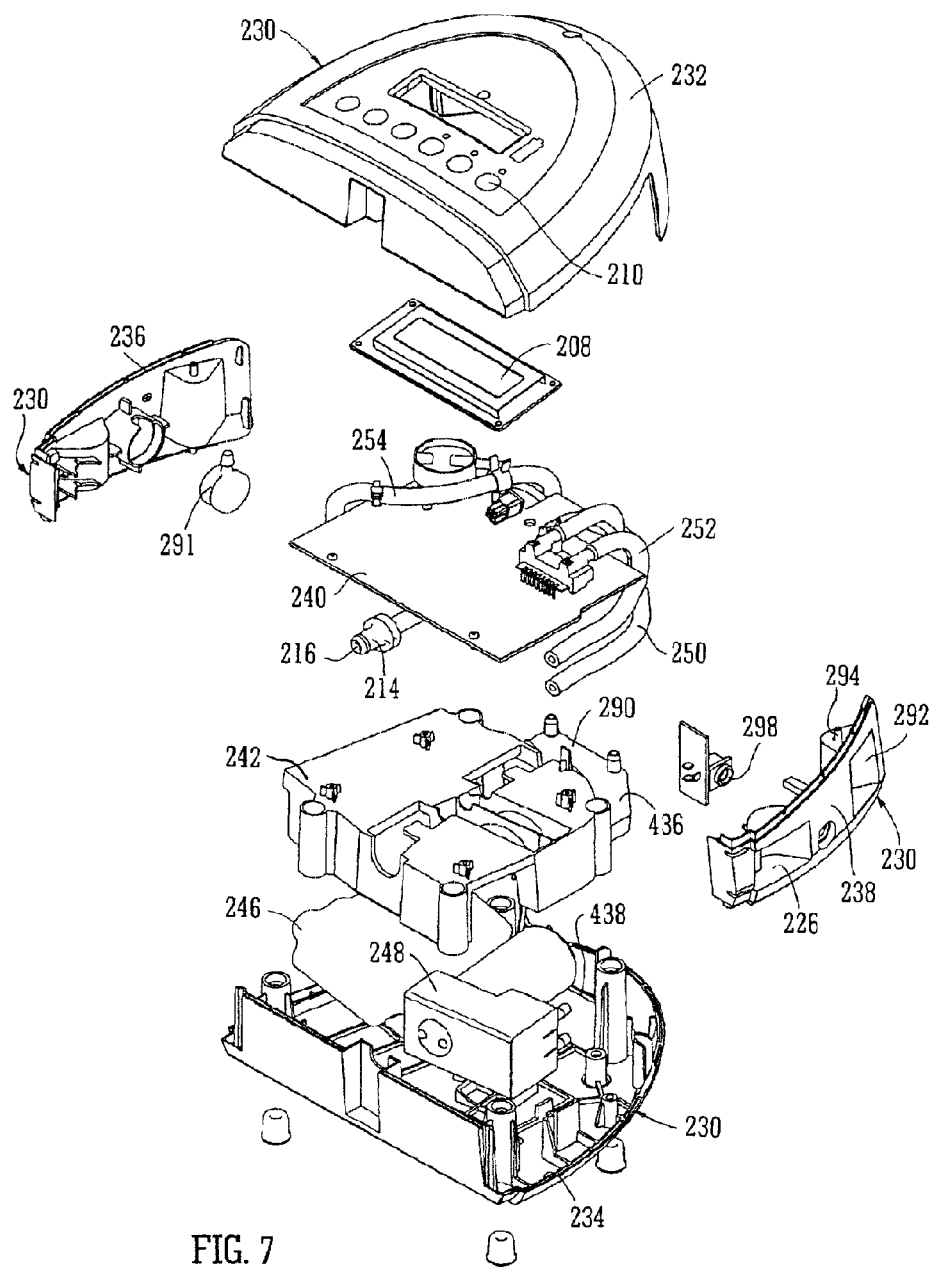
FIG. 7 shows an exploded view of the device unit of FIG. 6.
Figure 8:
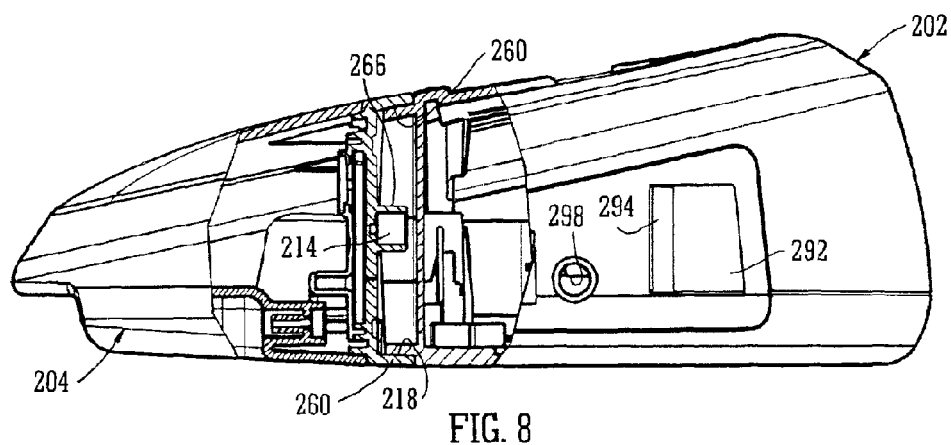
FIG. 8 shows a partially sectioned side elevation view through the interface between a waste canister and device unit of the apparatus.
Figure 9:
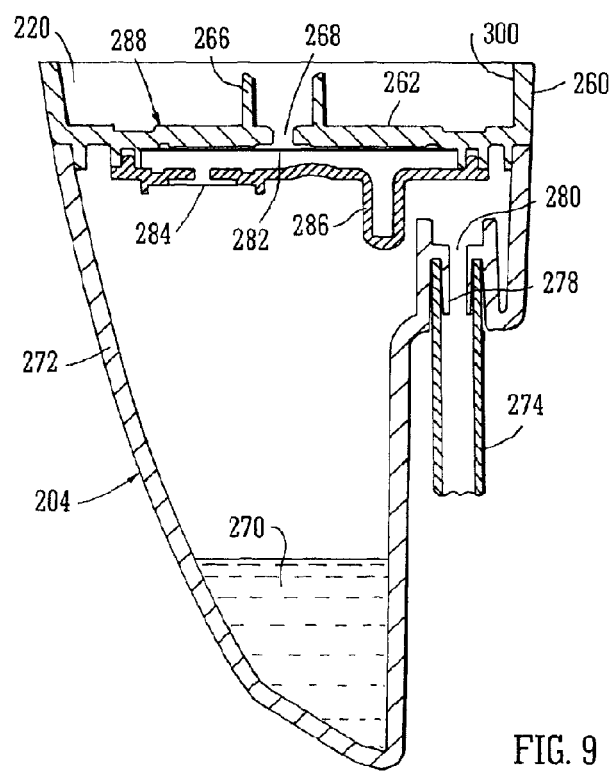
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 5:
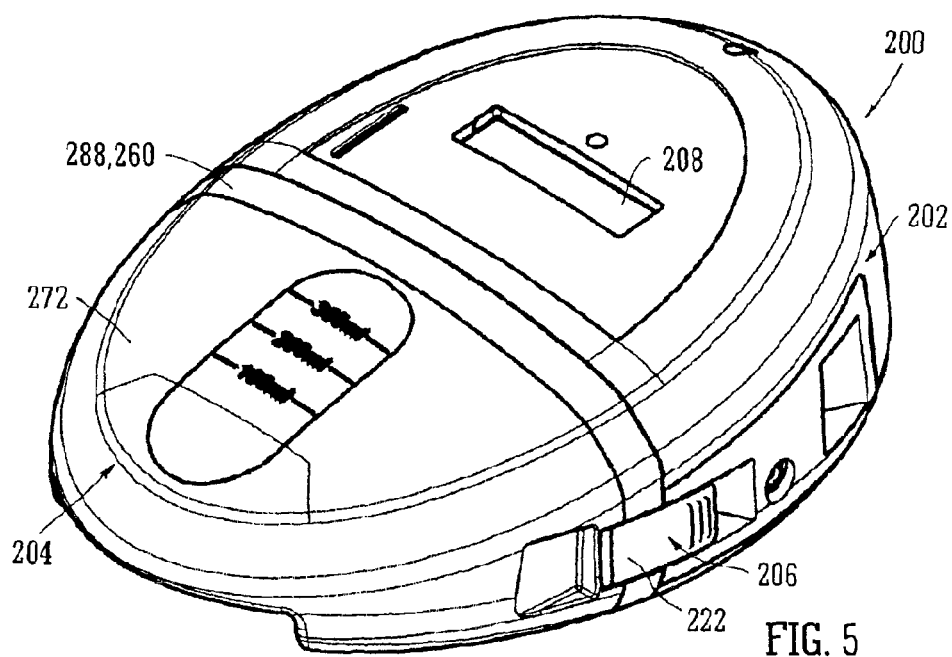
FIG. 5 shows a perspective view of an apparatus.
Figure 6:
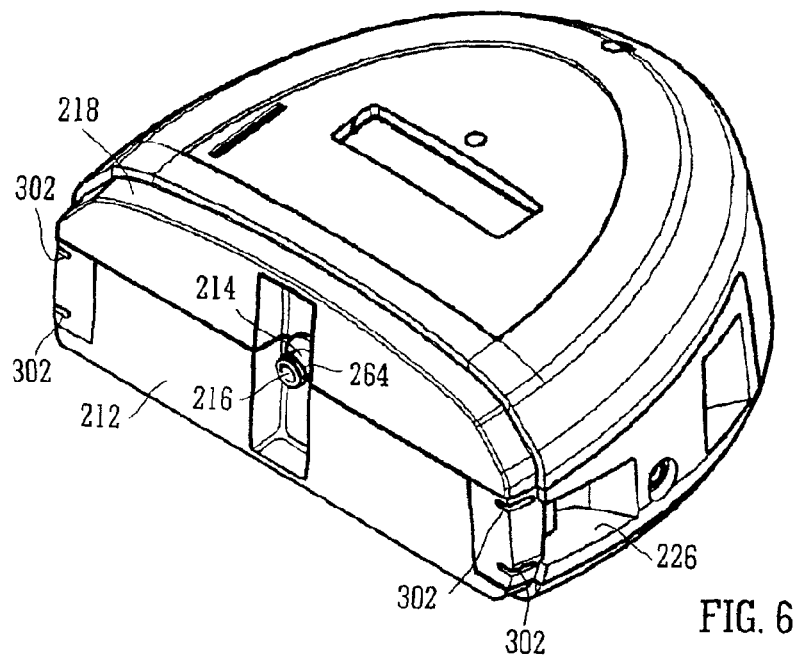
FIG. 6 shows a perspective view of an assembled device unit of the apparatus of FIG. 5.
Figure 10:
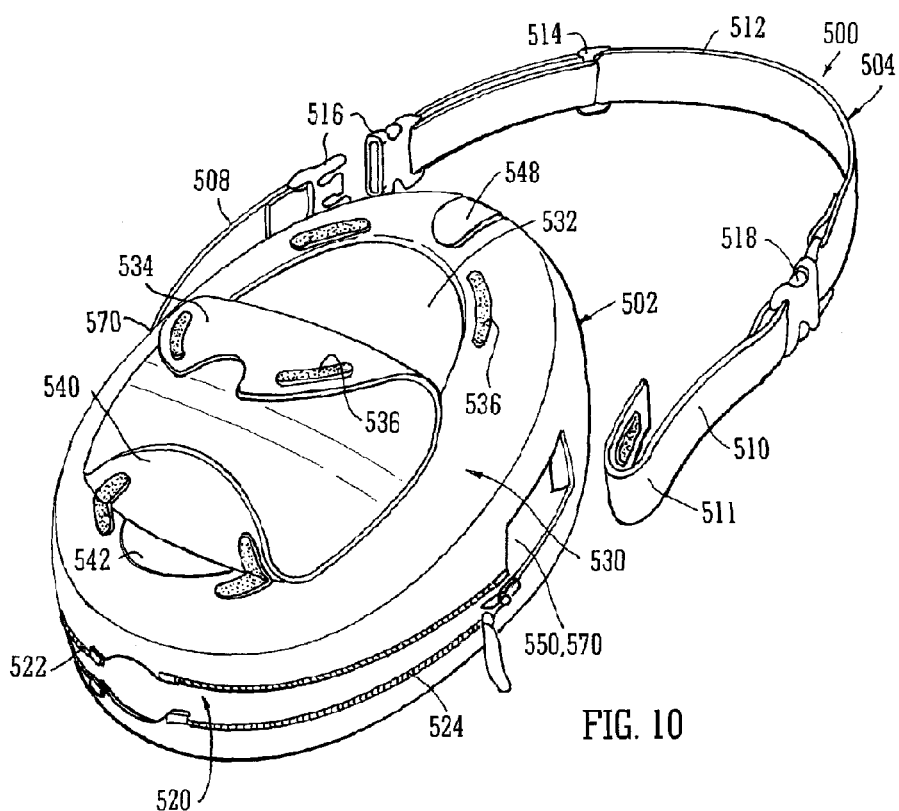
FIG. 10 shows a perspective view towards a front face and side portion of an embodiment of a carrying case and handle according to the present invention.
Figure 11:
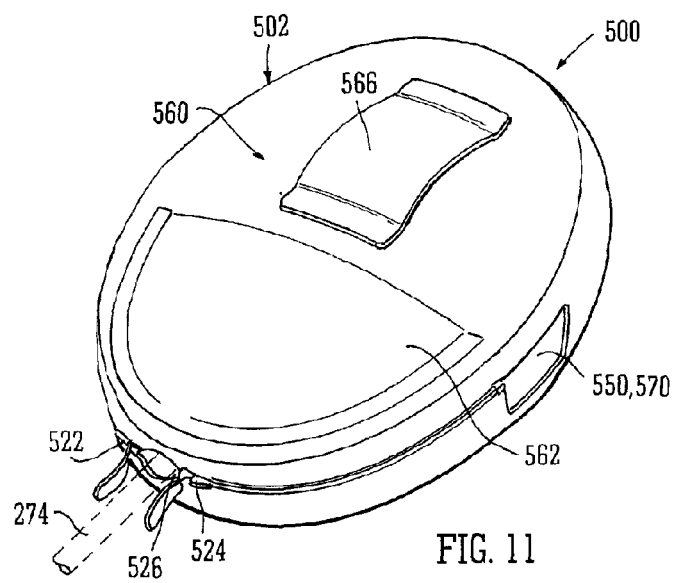
FIG. 11 shows the carrying case of FIG. 10 from a rear perspective.
Figure 12:
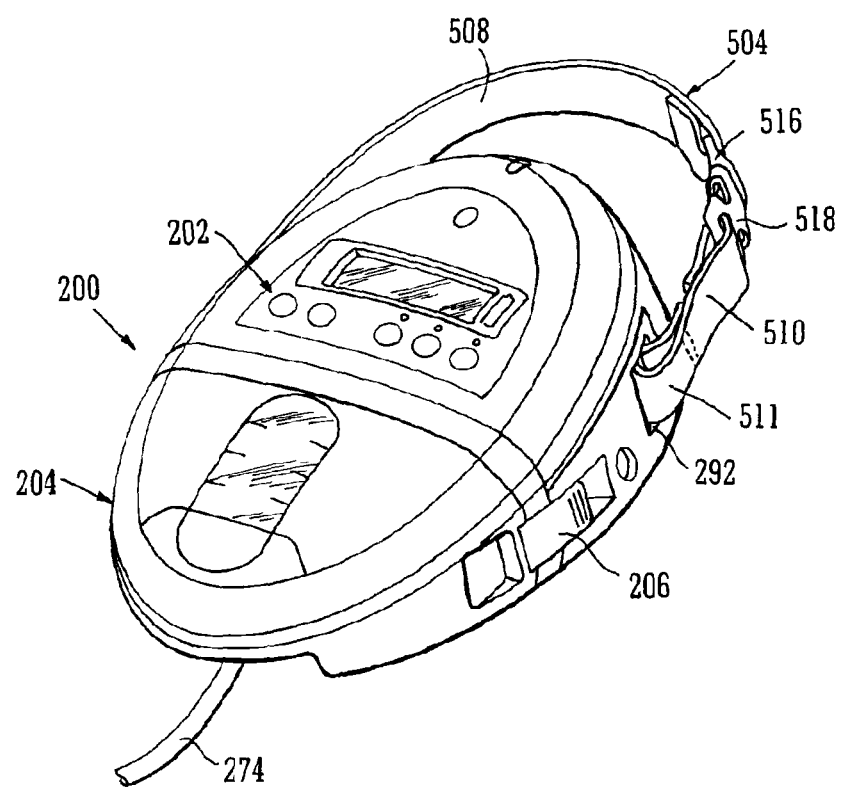
FIG. 12 which shows a perspective view of a device and waste canister having a handle according to an embodiment of the present invention attached thereto.

Referring now to FIGS. 10 to 12 where a carrying case 500 according to an embodiment of the present invention is shown and is for accommodating apparatus 200 comprising a connected device 202 and waste canister 204 as shown in FIG. 5. However, FIG. 5 does not show the aspiration conduit 274 (FIG. 9) which has been drawn into FIGS. 10 and 11 to show the position where it enters the carrying case 500. Reference is also made to FIG. 7 which shows parts of the device casing structure.

The carrying case 500 and strap comprises a pouch portion 502 for receiving the apparatus (not shown but see 200 in FIG. 5) and a carrying handle 504. The carrying handle 504 is divided into 3 portions: 2 short portions 508, 510 which are connected directly to the device by the support pins 294 in the recesses 292 in side pieces 236, 238 (see FIG. 7) by loops 511; and, a longer removable portion 512 which is itself adjustable in length by means of a sliding buckle 514. The longer handle portion 512 is joined to the shorter portions 508, 510 by squeeze buckles 516, 518 which are so arranged that the squeeze buckle portions at the ends of the shorter handle portions 508, 510 can be joined directly together to form a short handle for a user's hand if they so wish. The squeeze buckles described and shown may be replaced with any other type of easily manipulated connector. The pouch portion has a lower opening 520 through which the apparatus 200 may be inserted. The lower opening 520 is openable and closable by two zips 522, 524 which when closed leave an aperture 526 therebetween for the aspiration conduit 274 (shown as a dashed line in FIG. 11) to the waste canister to enter. The zips 522, 524 on the lower opening are able to open the lower opening sufficiently far to enable a user to easily gain access to the releasable catch arrangements 206 which secure the device 202 and waste canister 204 together (see FIG. 5) in order to release them for changing the waste canister. On a front face 530 of the pouch portion there is an upper clear window portion 532 formed from a flexible transparent plastics material and which is generally covered by a flap portion 534 releasably secured to the pouch portion 502 by hook and loop type material 536, for example and hinged at a lower edge thereof. The window portion 532 allows a user to see and access control buttons or a keypad on the device to vary the TNP therapy being applied by the apparatus, for example. A lower flap portion 540 is provided over a lower clear window portion 542 which coincides with the position of the waste canister so that the user may check on its filling condition. The lower flap portion 540 is also secured over the window 542 by hook and loop type material and is hinged at an upper edge thereof. A clear window aperture 548 is situated to coincide with a visible status indicator on the device. At a side portion of the pouch there is an aperture 550 which coincides with the position of a charging socket for a jack to recharge batteries carried within the device and also to coincide with an exhaust port for finally venting aspirated gaseous fluid to the atmosphere. A rear face 560 of the pouch 502 is provided with a pocket portion 562 for storing spares such as a new aspiration conduit (not shown), for example, or for storing excess aspiration conduit during use depending upon the position of the wound being treated. A belt loop 566 is also provided for users who particularly wish to use such a support means (a short carry handle comprising the two short portions 508, 510 will still be retained and attached directly to the device unit 202). Side apertures 570 are provided in the pouch to permit the short handle portions 508, 510 to pass therethrough. The side aperture 570 on the side of the charging socket and exhaust of the device may coincide with aperture 550.

FIG. 12 shows the apparatus 200 having the carrying handle of the present invention attached to it prior to insertion into the pouch 502. The two short handle portions are connected together by the squeeze buckles 508, 510, the centre portion 512 having been removed. When the apparatus 200 is inserted into the pouch via the lower opening 520, the buckles 516, 518 are first disconnected and passed through the openings, 550, 570 before being reconnected.

With the carrying bag according to the present invention a full waste canister may be changed easily by opening the lower opening 520 which allows access to the securing clips 206 between the device and waste canister so that the waste canister may be removed and a fresh one installed without fear of the device falling to the ground. Because of the carrying handle 504 being connected directly to the device at the support pins 294, the apparatus is perfectly secure whilst the lower aperture 520 is open. Because the apparatus 200 is completely enclosed except for the conduit 274 the type and purpose of the apparatus is not immediately apparent to casual observers.

Even if the apparatus is being carried in the pouch using the belt loop 560 the apparatus cannot fall out through the lower opening 520 even if open so long as the buckles 516, 518 are connected.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A carrying case for a negative pressure therapy apparatus comprising:
    a flexible pouch configured to at least partially enclose the apparatus and to conform to a shape of the apparatus, the pouch comprising a left side panel, a right side panel, a front side panel, and a rear side panel;
    an opening in a bottom portion of the pouch, the opening configured to permit insertion of the apparatus into the pouch;
    a closure positioned on at least one of the left or right side panels of the pouch, the closure positioned toward the rear side panel of the pouch in relation to a middle of the at least one of the left or right side panels, the closure configured to be opened and closed, wherein when the closure is open, the apparatus can be inserted into the pouch and when the closure is closed, the apparatus is prevented from being displaced from the pouch;
    an aperture between an interior and exterior of the pouch, the aperture sized to pass through the aperture a conduit configured to provide fluidic communication between the negative pressure therapy apparatus and a wound, wherein the aperture is aligned with the closure and the aperture remains open when the closure is closed;
    a first window panel configured to permit viewing of a first portion of the apparatus; and
    a second window panel configured to permit viewing of a second portion of the apparatus different from the first portion of the apparatus.

2. The carrying case of claim 1, further comprising at least one additional opening in the at least one of the left or right side panels the pouch configured to permit an attachment to be attached directly to the apparatus.

3. The carrying case of claim 1, wherein the closure comprises a first closure portion and a second closure portion, and wherein the aperture is located between the first and second closure portions.

4. The carrying case of claim 1, wherein at least one of the first or second window panels comprises a flap configured to be moved to permit viewing of at least a portion of the apparatus.

5. The carrying case of claim 1, further comprising a viewing panel in the pouch coinciding with a position of a visual indicator placed on a surface of the apparatus, the viewing panel configured to permit viewing of the visual indicator.

6. The carrying case of claim 1, wherein the closure comprises a zipper, a magnetic closure, press studs, or a Velcro fastener.

7. The carrying case of claim 1, further comprising a pocket portion on the rear side panel of the pouch, the pocket portion configured to accommodate spare equipment.

8. The carrying case of claim 1, further comprising a support loop on the rear side panel of the pouch, the support loop configured to be attached to a belt.

9. The carrying case of claim 1, further comprising a plurality of side openings positioned in at least one of the left or right side panels of the pouch.

10. The carrying case of claim 9, in combination with an attachment configured to be directly attached to the apparatus using the plurality of side openings.

11. The carrying case of claim 1, wherein when the closure does not close the opening, the pouch is further configured to permit removal of a portion of the apparatus from the bottom portion of the pouch while a remainder of the apparatus continues to be at least partially enclosed in a top portion of the pouch.

12. The carrying case of claim 1, wherein the aperture is sized to permit the conduit to extend outside of the pouch when the opening is closed by the closure.

13. The carrying case of claim 1, wherein the aperture is formed between edges of the closure.

14. The carrying case of claim 10, wherein the attachment comprises a carrying strap.

15. The carrying case of claim 1, wherein:
    a top portion of the pouch is sized to at least partially enclose a device unit of the negative pressure therapy apparatus and the bottom portion of the pouch is sized to at least partially enclose a waste canister of the negative pressure therapy apparatus,
    the waste canister is removably attached to the device unit, and the waste canister is configured to store fluid aspirated from the wound and the conduit is attached to the waste canister, and
    the device unit comprises a housing, a negative pressure source positioned in the housing, and a user interface positioned on an exterior surface of the housing.

16. The carrying case of claim 15, wherein the first window panel is configured to selectively permit viewing of the waste canister.

17. The carrying case of claim 16, wherein the second window panel is configured to selectively permit viewing of the user interface.

18. The carrying case of claim 15, wherein when the closure is not closed, the pouch is further configured to permit removal of the waste canister from the bottom portion of the pouch and replacement of the waste canister while the device unit continues to be at least partially enclosed in the top portion of the pouch.

19. The carrying case of claim 9, wherein the plurality of side openings are positioned to permit accessing a plurality of supports positioned on an exterior of the apparatus.

20. The carrying case of claim 1, wherein:
    the closure comprises a first closure positioned along the left side panel of the bottom portion of the pouch and a second closure positioned along the right side panel of the bottom portion of the pouch,
    the aperture is positioned between the first and second closures, and
    a center of the aperture is aligned with the first and second closures.

21. A carrying case for a negative pressure therapy apparatus comprising:
    a flexible pouch configured to at least partially enclose the apparatus and to conform to a shape of the apparatus, the pouch comprising a left side panel, a right side panel, a front side panel, and a rear side panel;
    an opening in a bottom portion of the pouch, the opening configured to permit insertion of the apparatus into the pouch;
    a closure positioned on at least one of the left or right side panels of the pouch, the closure positioned toward the rear side panel of the pouch in relation to a middle of the at least one of the left or right side panels, the closure configured to be opened and closed, wherein when the closure is open, the apparatus can be inserted into the pouch and when the closure is closed, the apparatus is prevented from being displaced from the pouch;

an aperture between an interior and exterior of the pouch, the aperture sized to pass through the aperture a conduit configured to provide fluidic communication between the negative pressure therapy apparatus and a wound, wherein the aperture is aligned with the closure and the aperture remains open when the closure is closed; and a plurality of side openings positioned on at least one of the left or right side panels of the pouch.

22. The carrying case of claim 21, wherein the plurality of side openings are positioned to permit accessing a plurality of supports positioned on an exterior of the apparatus the plurality of supports configured to be attached to an attachment.

23. A carrying case for a negative pressure therapy apparatus comprising:

a flexible pouch configured to at least partially enclose the apparatus and to conform to a shape of the apparatus, the pouch comprising a left side panel, a right side panel, a front side panel, and a rear side panel, wherein a top portion of the pouch is sized to at least partially enclose a device unit of the negative pressure therapy apparatus and a bottom portion of the pouch is sized to at least partially enclose a waste canister of the negative pressure therapy apparatus;

an opening in the bottom portion of the pouch, the opening configured to permit insertion of the apparatus into the pouch;

a closure positioned on at least one of the left or right side panels of the pouch, the closure positioned toward the rear side panel of the pouch in relation to a middle of the at least one of the left or right side panels, the closure configured to be opened and closed, wherein when the closure is open, the apparatus can be inserted into the pouch and when the closure is closed, the apparatus is prevented from being displaced from the pouch;

an aperture between an interior and exterior of the pouch, the aperture sized to pass through the aperture a conduit configured to provide fluidic communication between the negative pressure therapy apparatus and a wound, wherein the aperture is aligned with the closure and the aperture remains open when the closure is closed; and a first window panel placed in the bottom portion of the pouch, the first window panel configured to selectively permit viewing of the waste canister, wherein the waste canister is removably attached to the device unit, and the waste canister is configured to store fluid aspirated from the wound and the conduit is attached to the waste canister, and wherein the device unit comprises a housing, a negative pressure source positioned in the housing, and a user interface positioned on an exterior surface of the housing.

24. The carrying case of claim 23, further comprising a second window panel placed in the top portion of the pouch, the second window panel configured to selectively permit viewing of the user interface.

25. A carrying case for a negative pressure therapy apparatus comprising:

a flexible pouch configured to at least partially enclose the apparatus and to conform to a shape of the apparatus, the pouch comprising a left side panel, a right side panel, a front side panel, and a rear side panel, wherein a top portion of the pouch is sized to at least partially enclose a device unit of the negative pressure therapy apparatus and a bottom portion of the pouch is sized to at least partially enclose a waste canister of the negative pressure therapy apparatus;

an opening in the bottom portion of the pouch, the opening configured to permit insertion of the apparatus into the pouch;

a closure positioned on at least one of the left or right side panels of the pouch, the closure positioned toward the rear side panel of the pouch in relation to a middle of the at least one of the left or right side panels, the closure configured to be opened and closed, wherein when the closure is open, the apparatus can be inserted into the pouch and when the closure is closed, the apparatus is prevented from being displaced from the pouch;

an aperture between an interior and exterior of the pouch, the aperture sized to pass through the aperture a conduit configured to provide fluidic communication between the negative pressure therapy apparatus and a wound, wherein the aperture is aligned with the closure and the aperture remains open when the closure is closed; and a second window panel placed in the top portion of the pouch, the second window panel configured to selectively permit viewing of the user interface, wherein the waste canister is removably attached to the device unit, and the waste canister is configured to store fluid aspirated from the wound and the conduit is attached to the waste canister, and wherein the device unit comprises a housing, a negative pressure source positioned in the housing, and a user interface positioned on an exterior surface of the housing.

26. The carrying case of claim 25, further comprising a second window panel placed in the bottom portion of the pouch, the second window panel configured to selectively permit viewing of the waste canister.

* * * * *